United States Patent
Chamberlin et al.

(10) Patent No.: US 9,201,015 B2
(45) Date of Patent: Dec. 1, 2015

(54) PLATED THROUGH HOLE VOID DETECTION IN PRINTED CIRCUIT BOARDS BY DETECTING A PH-SENSITIVE COMPONENT

(75) Inventors: Bruce John Chamberlin, Vestal, NY (US); Chang-Min Chu, Taipei (TW); Gao-Bin Hu, ShenZhen (CN); Joseph Kuczynski, Rochester, MN (US); Kaspar Ka Chung Tsang, Tung Chung (HK)

(73) Assignee: International Business Machines Corporation, Armonk, NY (US)

( * ) Notice: Subject to any disclaimer, the term of this patent is extended or adjusted under 35 U.S.C. 154(b) by 1134 days.

(21) Appl. No.: 13/182,906

(22) Filed: Jul. 14, 2011

(65) Prior Publication Data

US 2013/0016465 A1 Jan. 17, 2013

(51) Int. Cl.
*B32B 7/00* (2006.01)
*G01N 21/80* (2006.01)
(Continued)

(52) U.S. Cl.
CPC .............. *G01N 21/80* (2013.01); *H05K 1/0269* (2013.01); *H05K 3/22* (2013.01); *H05K 3/42* (2013.01); *Y10T 29/49004* (2015.01)

(58) Field of Classification Search
CPC ............ G01B 11/20; G01B 5/30; G01B 7/16; G01L 1/225; G01N 21/91; G01N 2021/6439; C09K 11/06; C09K 2211/1029
USPC ................................ 73/762, 769; 252/301.19
See application file for complete search history.

(56) References Cited

U.S. PATENT DOCUMENTS

RE26,888 E     5/1970   Alburger
3,698,821 A   10/1972   Ekstrand ....................... 356/237
(Continued)

FOREIGN PATENT DOCUMENTS

EP     1 163 389     12/2009    ............... C08K 5/00
JP       63251110    10/1998    ............... B23B 49/00

OTHER PUBLICATIONS

Final Office Action for U.S. Appl. No. 13/182,611 (Chamberlin et al., "Plated Through Hole Void Detection in Printed Circuit Boards by Detecting Material Coupling to Exposed Laminate," filed Jul. 14, 2011), U.S. Patent and Trademark Office, mailed Sep. 10, 2013, 9 pages.

(Continued)

*Primary Examiner* — Humera Sheikh
*Assistant Examiner* — Seth Dumbris
(74) *Attorney, Agent, or Firm* — VanLeeuwen & VanLeeuwen; Diana R. Gerhardt

(57) ABSTRACT

An approach is provided in which a pH-indicating compound is incorporated in a printed circuit board. The printed circuit board includes a number of layers with the pH-sensitive indicator being incorporated in one of the layers. Conductive pathways are formed from a conductive sheet laminated onto an outer surface of the printed circuit board. The printed circuit board is exposed to a pH-activating solution. Plated-through hole defects in the printed circuit board are identified by detecting a color formation at a surface location of the printed circuit board that corresponds to the plated-through hole defect. Another approach is also provided where a pH-activating compound is incorporated in one of the layers of the printed circuit board which is then exposed to a pH-indicating solution to produce the color formation that identifies the location of the plated-through hole defect.

11 Claims, 6 Drawing Sheets

(51) Int. Cl.
*H05K 1/02* (2006.01)
*H05K 3/22* (2006.01)
*H05K 3/42* (2006.01)

(56) References Cited

U.S. PATENT DOCUMENTS

| | | | |
|---|---|---|---|
| 3,716,421 | A | 2/1973 | Burkhart et al. |
| 3,803,485 | A | 4/1974 | Crites et al. |
| 3,808,434 | A | 4/1974 | Gutbier |
| 3,840,802 | A | 10/1974 | Anthony |
| 4,002,905 | A | 1/1977 | Molina |
| 4,400,618 | A | 8/1983 | Bupp et al. ............ 250/302 |
| 4,477,484 | A | 10/1984 | Paoletti et al. |
| 4,560,273 | A | 12/1985 | Ando et al. ............ 356/237 |
| 4,697,923 | A | 10/1987 | Jones et al. |
| 4,746,751 | A | 5/1988 | Oviatt, Jr. et al. ........ 556/456 |
| 4,766,325 | A | 8/1988 | Merkenschlager et al. ... 250/572 |
| 4,774,188 | A | 9/1988 | Chandross |
| 4,799,175 | A | 1/1989 | Sano et al. ............ 364/552 |
| 4,930,890 | A | 6/1990 | Hara et al. ............ 356/241.1 |
| 5,040,047 | A * | 8/1991 | Cole et al. ............ 257/642 |
| 5,070,158 | A * | 12/1991 | Holloway et al. ........ 525/475 |
| 5,120,339 | A | 6/1992 | Markovich et al. ........ 65/3.1 |
| 5,216,479 | A | 6/1993 | Dotan et al. |
| 5,314,740 | A | 5/1994 | Ishii et al. ............ 428/209 |
| 5,376,189 | A * | 12/1994 | Kukanskis ............ 148/269 |
| 5,707,434 | A | 1/1998 | Halloran et al. ........ 106/287.11 |
| 6,084,663 | A | 7/2000 | Seng ............ 356/237.4 |
| 6,187,417 | B1 | 2/2001 | Farquhar et al. |
| 6,194,085 | B1 | 2/2001 | Fasano et al. |
| 6,384,911 | B1 | 5/2002 | Wang et al. ............ 356/237.6 |
| 6,506,314 | B1 | 1/2003 | Whitney, Jr. et al. ......... 216/100 |
| 6,684,172 | B1 | 1/2004 | Subramanian et al. |
| 7,172,818 | B2 | 2/2007 | Nakaoka et al. ............ 428/553 |
| 7,498,520 | B2 | 3/2009 | Osaka et al. ............ 174/250 |
| 2001/0002935 | A1 | 6/2001 | Greenberg et al. ............ 382/147 |
| 2002/0019464 | A1 | 2/2002 | Hein et al. ............ 523/461 |
| 2002/0034825 | A1 * | 3/2002 | Schweigart ............ 436/100 |
| 2004/0037966 | A1 | 2/2004 | Yokochiro et al. |
| 2005/0110149 | A1 | 5/2005 | Osaka et al. ............ 257/758 |
| 2012/0194810 | A1 | 8/2012 | Kim et al. |

OTHER PUBLICATIONS

Wencel et al., "Novel sol-gel derived films for luminescence-based oxygen and pH sensing," Materials Science—Poland, vol. 25, No. 3, 2007.

Lim et al., "A colorimetric sensor array of porous pigments," Analyst, Dec. 2009, 134(12): 2453-2457.

Li et al., "Self-assembly of bridged silsesquioxanes incorporated with conjugated organic functionalities," Frontiers of Chemistry in China, vol. 5, No. 3, 2005.

Office Action for U.S. Appl. No. 13/182,611 (Chamberlin et al., "Plated Through Hole Void Detection in Printed Circuit Boards by Detecting Material Coupling to Exposed Laminate," filed Jul. 14, 2011), U.S. Patent and Trademark Office, mailed May 1, 2013, 9 pages.

Notice of Allowance for U.S. Appl. No. 14/088,107 (Chamberlin et al., "Plated Through Hole Void Detection in Printed Circuit Boards by Detecting a pH-Sensitive Component," filed Nov. 22, 2013), U.S. Patent and Trademark Office, mailed Oct. 1, 2015, 15 pages.

* cited by examiner

PLATED THROUGH HOLE VOID DETECTION IN PRINTED CIRCUIT BOARDS BY DETECTING A PH-SENSITIVE COMPONENT

BACKGROUND

The present invention relates to an approach that detects plated through hole voids in printed circuit boards using a pH-sensitive component included in the laminate of the circuit board or in an acid or base to which the an indicator bonds.

Plated through hole voids are a known issue when manufacturing printed circuit boards (PCB). Plated through hole voids may potentially cause failure during assembly and are also considered as a long term reliability issue of the printed circuit boards. Current understanding of the phenomenon indicates that the voids typically form during composite copper plating before external circuitization. For example, voids may form if the copper plating solution was blocked by air bubbles, foreign material, or dry film resist residues. During that period, the entire PCB is virtually encased in copper. The only areas where laminate would be exposed is at a defect site where there is a void in the copper. This defect is difficult to detect using currently-available inspection capability or test equipment. The voids may not entirely encircle the hole wall and thus may not result in an electrical open thereby making it difficult to detect by an electrical method. In the subsequent card assembly and field application processes, these voids may become an intermittent open, or even a dead open, due to high thermal stress in the assembly process or temperature cycling during the application stage.

BRIEF SUMMARY

An approach is provided in which a pH-indicating compound is incorporated in a printed circuit board. The printed circuit board includes a number of layers with the pH-sensitive indicator being incorporated in one of the layers. Conductive pathways are formed from a conductive sheet laminated onto an outer surface of the printed circuit board. The printed circuit board is exposed to a pH-activating solution. Plated-through hole defects in the printed circuit board are identified by detecting a color formation at a surface location of the printed circuit board that corresponds to the plated-through hole defect.

Another approach is also provided in which a pH-activating compound is incorporated in the printed circuit board that includes a number of layers. The pH-sensitive activator is incorporated in one of the layers. Conductive pathways are formed from a conductive sheet laminated onto an outer surface of the printed circuit board. The printed circuit board is exposed to a pH-indicating solution. Plated-through hole defects in the printed circuit board are identified by detecting a color formation at a surface location of the printed circuit board that corresponds to the plated-through hole defect.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE SEVERAL VIEWS OF THE DRAWINGS

The present invention may be better understood, and its numerous objects, features, and advantages made apparent to those skilled in the art by referencing the accompanying drawings, wherein.

DETAILED DESCRIPTION

Figure 1:
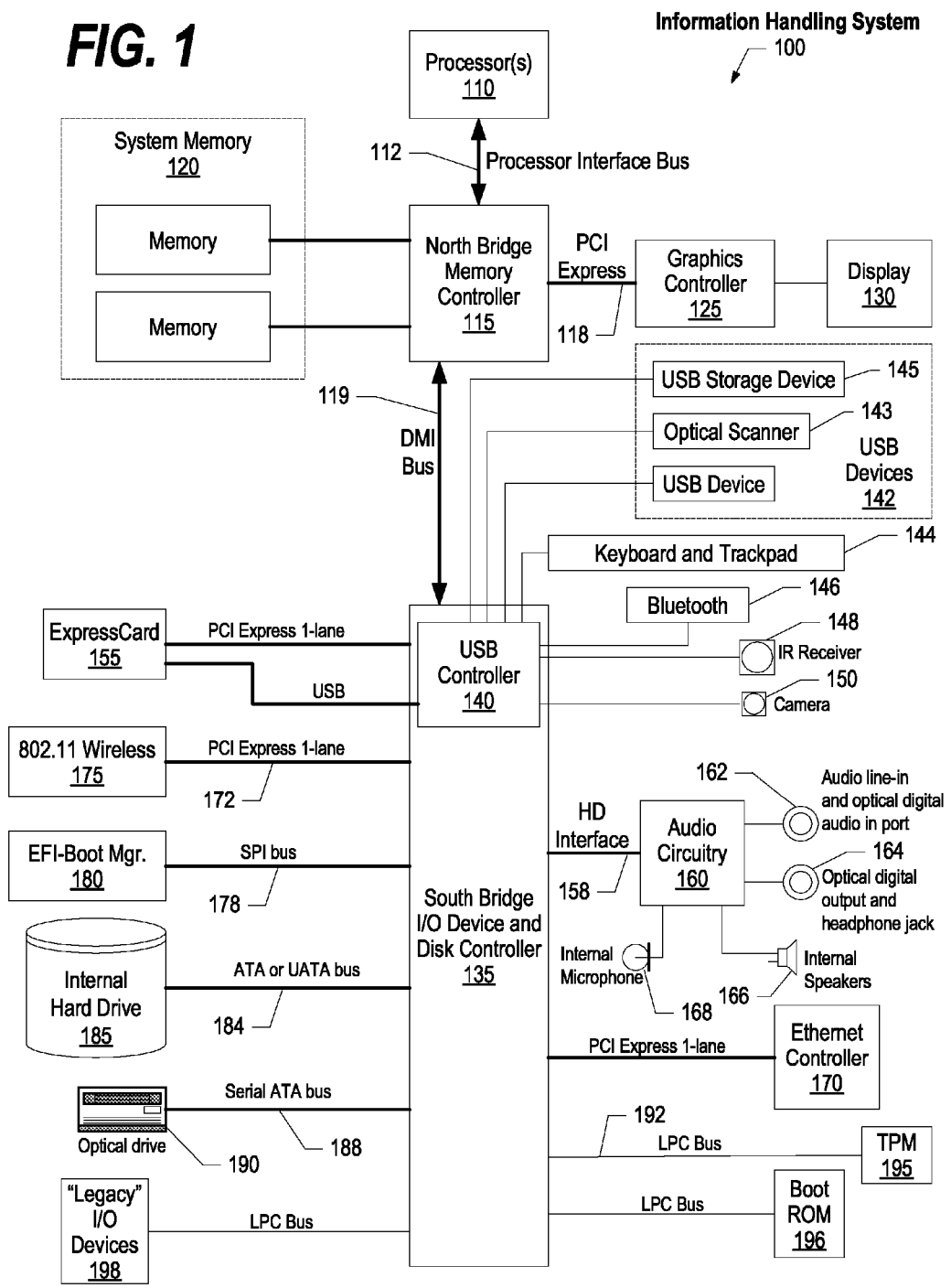
FIG. 1 is a block diagram of a data processing system in which the methods described herein can be implemented.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The following detailed description will generally follow the summary of the invention, as set forth above, further explaining and expanding the definitions of the various aspects and embodiments of the invention as necessary. To this end, this detailed description first sets forth a computing environment in FIG. 1 that is suitable to implement the software and/or hardware techniques associated with the invention. In addition, many of the components of an information system, such as motherboards, video cards, network cards, etc., include printed circuit boards. Such printed circuit boards can be manufactured using the invention described herein. A networked environment is illustrated in FIG. 2 as an extension of the basic computing environment, to emphasize that modern computing techniques can be performed across multiple discrete devices.

Figure 2:
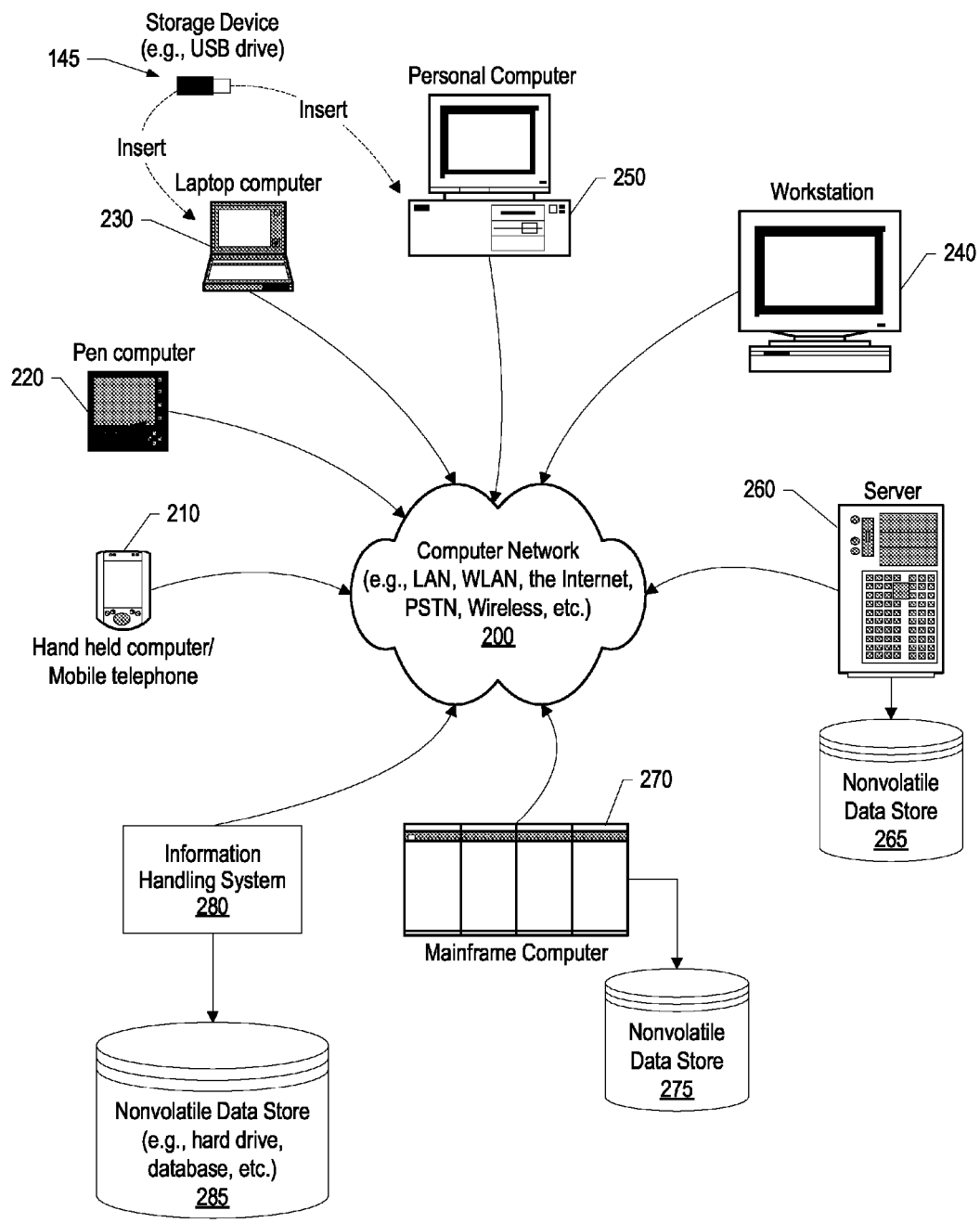
FIG. 2 provides an extension of the information handling system environment shown in FIG. 1 to illustrate that the methods described herein can be performed on a wide variety of information handling systems which operate in a networked environment.

FIG. 1 illustrates information handling system 100, which is a simplified example of a computer system capable of performing the computing operations described herein. In addition, as noted above, many of the components of information handling system 100 include printed circuit boards. Such components include, but are not limited to motherboards, video cards, network cards, etc., and may be manufactured using the present invention. Further note that information handling system 100 can be part of a larger computer system including a network of interconnected systems, and that many of the components in such interconnected systems may include printed circuit boards manufactured according to present invention. Information handling system 100 includes one or more processors 110 coupled to processor interface bus 112. Processor interface bus 112 connects processors 110 to Northbridge 115, which is also known as the Memory Controller Hub (MCH). Northbridge 115 connects to system memory 120 and provides a means for processor(s) 110 to access the system memory. Graphics controller 125 also connects to Northbridge 115. In one embodiment, PCI Express bus 118 connects Northbridge 115 to graphics controller 125. Graphics controller 125 connects to display device 130, such as a computer monitor.

Northbridge 115 and Southbridge 135 connect to each other using bus 119. In one embodiment, the bus is a Direct Media Interface (DMI) bus that transfers data at high speeds in each direction between Northbridge 115 and Southbridge 135. In another embodiment, a Peripheral Component Interconnect (PCI) bus connects the Northbridge and the Southbridge. Southbridge 135, also known as the I/O Controller Hub (ICH) is a chip that generally implements capabilities that operate at slower speeds than the capabilities provided by the Northbridge. Southbridge 135 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 196 and "legacy" I/O devices (using a "super I/O" chip). The "legacy" I/O devices (198) can include, for example, serial and parallel ports, keyboard, mouse, and/or a floppy disk controller. The LPC bus also connects Southbridge 135 to Trusted Platform Module (TPM) 195. Other components often included in Southbridge 135 include a Direct Memory Access (DMA) controller, a Programmable Interrupt Controller (PIC), and a storage device controller, which connects Southbridge 135 to nonvolatile storage device 185, such as a hard disk drive, using bus 184.

ExpressCard 155 is a slot that connects hot-pluggable devices to the information handling system. ExpressCard 155 supports both PCI Express and USB connectivity as it connects to Southbridge 135 using both the Universal Serial Bus (USB) the PCI Express bus. Southbridge 135 includes USB Controller 140 that provides USB connectivity to devices that connect to the USB. These devices include webcam (camera) 150, infrared (IR) receiver 148, keyboard and trackpad 144, and Bluetooth device 146, which provides for wireless personal area networks (PANs). USB Controller 140 also provides USB connectivity to other miscellaneous USB connected devices 142, such as a mouse, removable nonvolatile storage device 145, modems, network cards, ISDN connectors, fax, printers, USB hubs, and many other types of USB connected devices. While removable nonvolatile storage device 145 is shown as a USB-connected device, removable nonvolatile storage device 145 could be connected using a different interface, such as a Firewire interface, etcetera.

Wireless Local Area Network (LAN) device 175 connects to Southbridge 135 via the PCI or PCI Express bus 172. LAN device 175 typically implements one of the IEEE 802.11 standards of over-the-air modulation techniques that all use the same protocol to wireless communicate between information handling system 100 and another computer system or device. Optical storage device 190 connects to Southbridge 135 using Serial ATA (SATA) bus 188. Serial ATA adapters and devices communicate over a high-speed serial link. The Serial ATA bus also connects Southbridge 135 to other forms of storage devices, such as hard disk drives. Audio circuitry 160, such as a sound card, connects to Southbridge 135 via bus 158. Audio circuitry 160 also provides functionality such as audio line-in and optical digital audio in port 162, optical digital output and headphone jack 164, internal speakers 166, and internal microphone 168. Ethernet controller 170 connects to Southbridge 135 using a bus, such as the PCI or PCI Express bus. Ethernet controller 170 connects information handling system 100 to a computer network, such as a Local Area Network (LAN), the Internet, and other public and private computer networks. Optical scanner 143 is a scanner that is capable of detecting color formations on an object, such as a printed circuit board (PCB). In the embodiment shown, the optical scanner is connected to the information handling system using one of the USB connections provided by USB Controller 140. Other embodiments may be utilized in which optical scanner 143 is included in the information handling system using a different interface provided by the information handling system.

While FIG. 1 shows one information handling system, an information handling system may take many forms. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

The Trusted Platform Module (TPM 195) shown in FIG. 1 and described herein to provide security functions is but one example of a hardware security module (HSM). Therefore, the TPM described and claimed herein includes any type of HSM including, but not limited to, hardware security devices that conform to the Trusted Computing Groups (TCG) standard, and entitled "Trusted Platform Module (TPM) Specification Version 1.2." The TPM is a hardware security subsystem that may be incorporated into any number of information handling systems, such as those outlined in FIG. 2.

FIG. 2 provides an extension of the information handling system environment shown in FIG. 1 to illustrate that the methods described herein can be performed on a wide variety of information handling systems that operate in a networked environment. Types of information handling systems range from small handheld devices, such as handheld computer/mobile telephone 210 to large mainframe systems, such as mainframe computer 270. Examples of handheld computer 210 include personal digital assistants (PDAs), personal entertainment devices, such as MP3 players, portable televisions, and compact disc players. Other examples of information handling systems include pen, or tablet, computer 220, laptop, or notebook, computer 230, workstation 240, personal computer system 250, and server 260. Other types of information handling systems that are not individually shown in FIG. 2 are represented by information handling system 280. As shown, the various information handling systems can be networked together using computer network 200. Types of computer network that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 2 depicts separate nonvolatile data stores (server 260 utilizes nonvolatile data store 265, mainframe computer 270 utilizes nonvolatile data store 275, and information handling system 280 utilizes nonvolatile data store 285). The nonvolatile data store can be a component that is external to the various information handling systems or can be internal to one of the information handling systems. In addition, removable nonvolatile storage device 145 can be shared among two or more information handling systems using various techniques, such as connecting the removable nonvolatile storage device 145 to a USB port or other connector of the information handling systems.

Figure 3:
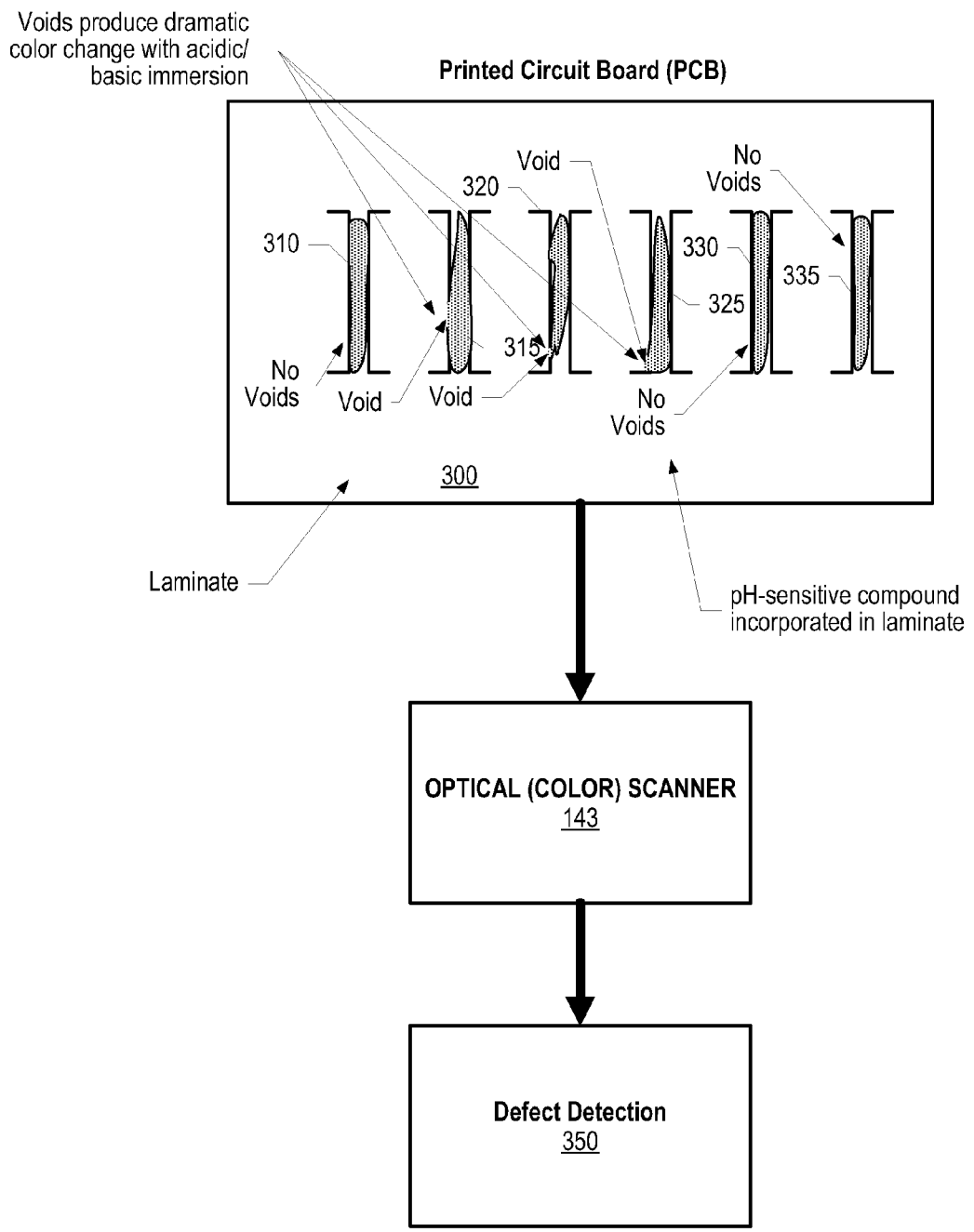
FIG. 3 is a diagram of a printed circuit board (PCB) with a variety of plated through hole voids shown in various circuits on the PCB that has a pH-sensitive indicator incorporated into the laminate.

FIG. 3 is a diagram of a printed circuit board (PCB) with a variety of plated through hole defects (voids) shown in various circuits on the PCB that has a pH-indicating compound incorporated into the laminate. Printed circuit board 300 is a circuit board that has been exposed to a pH-activating solution that forms a color formation at the locations of the plated-through hole defects when the pH-indicating compound reacts with the pH-activating solution. The pH-indicating compound and the pH-activating solution are chosen so that the pH-indicating compound reacts with the pH-activating solution. For example, if the pH-activating solution is a base solution, an appropriate pH-indicating solution that reacts to the base solution would be incorporated in one of the layers of the printed circuit board. Likewise, if the pH-activating solution is an acid solution, an appropriate pH-indicating solution that reacts to the acid solution would be incorporated in one of the layers of the printed circuit board. The term pH-non-neutral solution, as used herein, means a pH-activating solution that is either a base or an acid, with the appropriate pH-indicating compound being incorporated in one of the layers included in the printed circuit board.

A conductive sheet of material, such as a copper sheet, is laminated onto the outer surface of the PCB from which a number of conductive pathways (310, 315, 320, 325, 330, and 335) are formed on the PCB. In one embodiment, the conductive pathways are formed by etching the conductive sheet to form the pathways. After the conductive pathways are formed, the PCB is exposed to a pH-activating solution that is designed to change color when it contacts the pH-indicating compound that was incorporated in one of the PCB layers. In one embodiment, the PCB is exposed by immersing the PCB in the pH-activating solution.

The PCB is then scanned by color optical scanner 143 in order to detect any color formations caused by the pH-activating solution contacting the pH-indicating compound. The detection of a color formation identifies locations of plated-through-hole (PTH-void) defects in the PCB (defect detection 350).

In one embodiment, the pH-indicating compound is an indicator that reacts by forming a color change when contacted by a pH-non-neutral solution. The pH-indicating compound is incorporated into the laminate, either during formulation of the resin system or at some stage of the PCB laminate manufacturing process. After composite panel plating but prior to external circuitization, the entire PCB is encased in a thin copper sheet. Any exposed laminate (PTH void) will expose the pH-indicating compound. The PCB is then exposed to (e.g., immersed in, sprayed with, solutions run over, etc.) a pH-activating solution, such as an aqueous bath that contains an acid or base that reacts to the pH-indicating compound with the reaction forming a color change on the surface of the PCB. Any exposed laminate (PTH void) will cause a color change on the surface of the PCB when the pH-indicating compound comes in contact with the pH-activating solution. Through backlighting or some similar technique, the plated through holes can be scanned for a color change using optical scanner 143. In another embodiment, the pH-indicating component is an indicator that either shrinks or swells when contacted by a pH-non-neutral solution. Through backlighting or some similar technique, the plated through holes can be scanned for shrinkage and/or swelling using optical scanner 143.

Representative examples of suitable materials to use as the pH-indicating compound that is incorporated into the resin system are organically modified silicates (ormosils) containing a pH-sensitive dye such as those disclosed in "Novel sol-gel derived films for luminescence-based oxygen and pH sensing", Materials Science-Poland, Vol. 25, No. 3, 2007 and "A colorimetric sensor array of porous pigments", Analyst. 2009 December; 134(12): 2453-2457. These ormosils may be formulated directly into the resin system at suitable loading levels to produce the desired colorimetric response following immersion in an acidic/basic aqueous solution.

Figure 4:
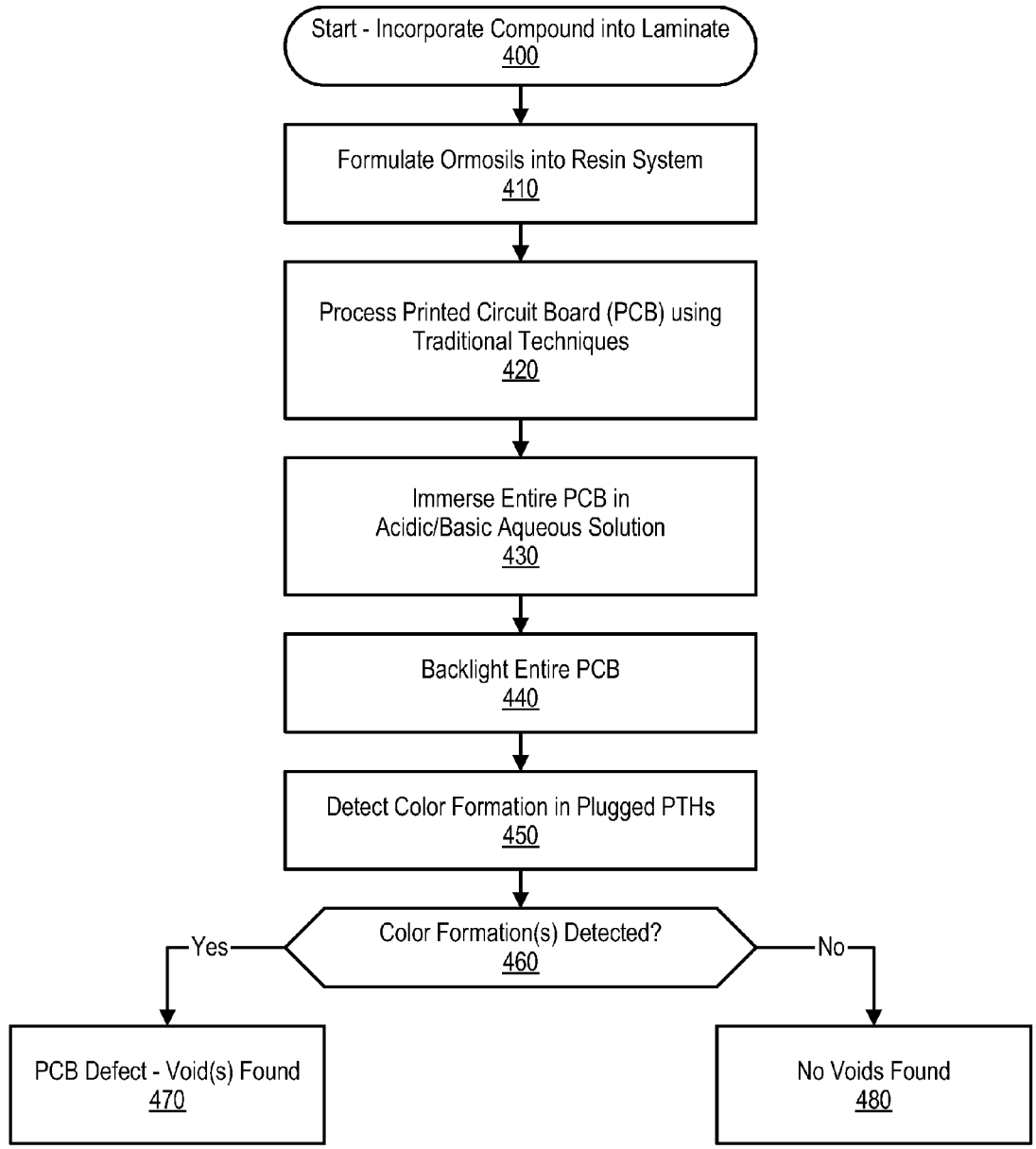
FIG. 4 is a flowchart showing steps taken to detect voids in a PCB that has a pH-sensitive indicator incorporated into the laminate as shown in FIG. 3.

FIG. 4 is a flowchart showing steps taken to detect defects in a printed circuit board (PCB) that has a pH-indicating compound incorporated into the laminate as shown in FIG. 3. Processing commences at 400 whereupon, at step 410, organically modified silicates (ormosils) are incorporated into the resin system of a PCB. Examples of ormosils that can be incorporated into the PCB were previously described in the description of FIG. 3. The ormosils are pH-indicating compounds that react when immersed in a pH-activating solution.

At step 420, the PCB, with the pH-indicating compound (e.g., ormosils, etc.) incorporated in at least one layer of the PCB, is processed using traditional techniques such as plating the PCB surface with a conductive sheet (e.g., copper, etc.) and forming conductive pathways from the conductive sheet (e.g., by etching the conductive sheet, etc.). At step 430, the PCB is exposed to a pH-activating solution. In one embodiment, the PCB is exposed to the pH-activating solution by immersing the entire PCB in a pH-activating solution, such as an acidic or basic aqueous solution. The pH-indicating compound (e.g., ormosils, etc.) that were incorporated in at least one layer of the PCB reacts when in contact with the pH-activating solution. The reaction causes a color formation to occur at the locations on the PCB where there are plated-through-hole (PTH) defects.

At step 440, the PCB is backlit using traditional backlighting techniques. At step 450, color formations in plugged PTHs are detected either manually (visually), or using an optical color scanner that is connected to an information handling system. A decision is made as to whether any color formations are detected indicating the presence of one or more plated-through hole defects (decision 460). If color formations are detected, then decision 460 branches to the "yes" branch whereupon, at step 470, the PCB is noted as being defective due to the presence of one or more plated-through-hole defects. On the other hand, if no color formations are detected, then decision 460 branches to the "no" branch whereupon, at step 480, the PCB is noted as not having any plated-through-hole defect.

Figure 5:
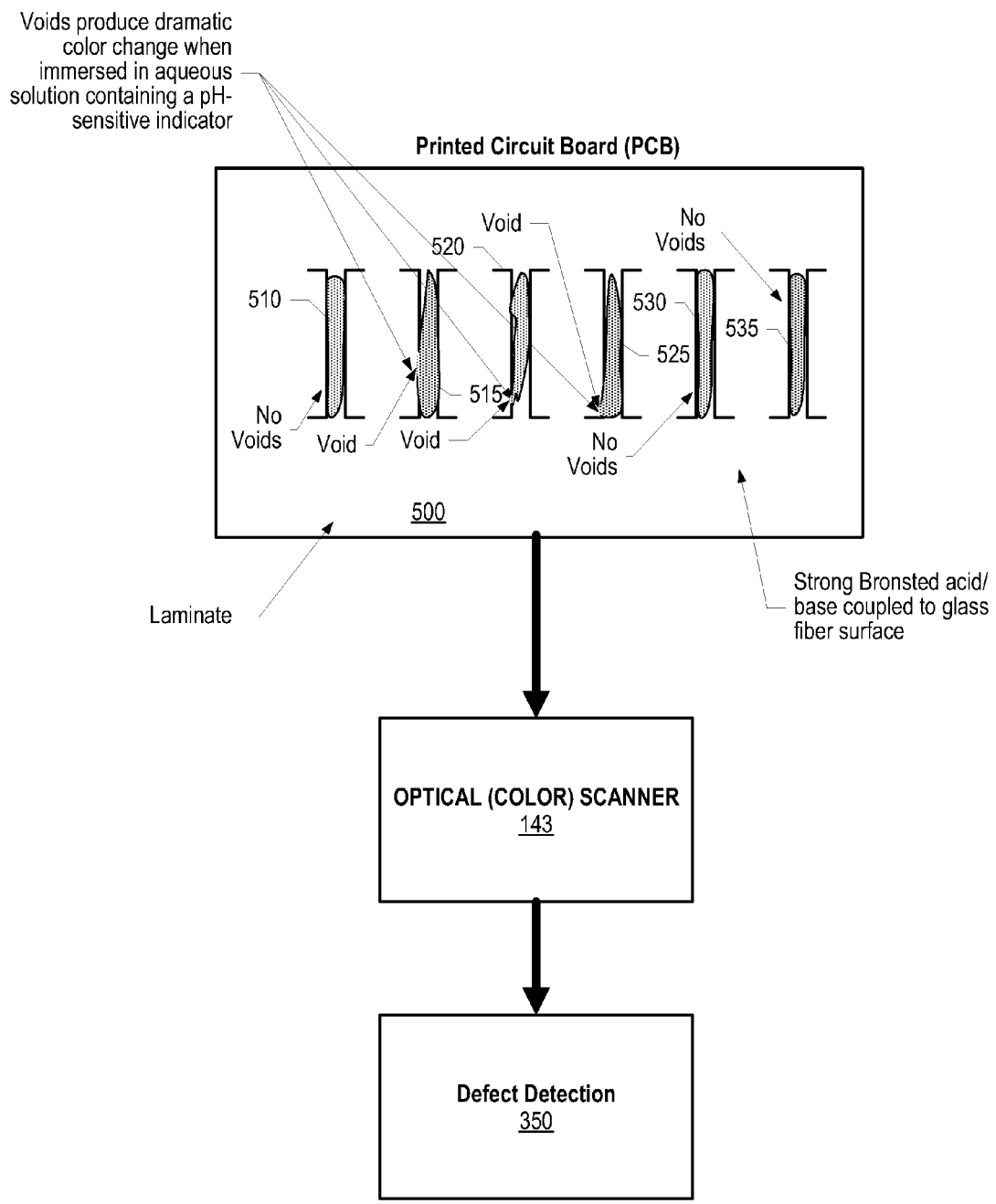
FIG. 5 is a diagram of a printed circuit board (PCB) with a variety of plated through hole voids shown in various circuits on the PCB that has a strong Bronsted acid or base coupled to the glass fiber surface of the PCB.

FIG. 5 is a of diagram a printed circuit board (PCB) with a variety of plated through hole voids shown in various circuits on the PCB that has pH-activating compound, such as a strong Bronsted acid or base, coupled to the glass fiber surface of the PCB. Printed circuit board 500 is a circuit board that has a strong Bronsted acid or base coupled with a glass layer included in the PCB. A conductive sheet of material, such as a copper sheet, is laminated onto the outer surface of the PCB from which a number of conductive pathways (510, 515, 520, 525, 530, and 535) are formed on the PCB. In one embodiment, the conductive pathways are formed by etching the conductive sheet to form the pathways. After the conductive pathways are formed, the PCB is exposed to a pH-indicating solution that is designed to change color when it contacts the strong Bronsted acid or base that was coupled to the glass fiber layer of the PCB. The pH-indicator from the solution bonds with the Bronsted acid or base, thus resulting in the color change. The term pH-non-neutral compound, as used herein, means a pH-activating compound that is either a base or an acid, with the PCB being exposed to an appropriate pH-indicating solution that reacts when in contact with the pH-non-neutral compound incorporated in one of the layers included in the printed circuit board.

The PCB is then scanned by color optical scanner 143 in order to detect any color formations caused by the pH-indicating solution contacting the pH-activating compound on the surface of the PCB. The detection of a color formation identifies locations of plated-through-hole (PTH-void) defects in the PCB (defect detection 550).

In the embodiment shown in FIG. 5, the pH-activating compound is a Bronsted acid or base that is incorporated into the glass fiber layer of PCB 500. After composite panel plating but prior to external circuitization, the entire PCB is encased in a thin copper sheet. Any exposed laminate (PTH void) will expose the pH-activating compound (e.g., the Bronsted acid or base). The PCB is then exposed to a pH-indicating solution, such as an aqueous bath that includes a pH-sensitive indicator. In one embodiment, the PCB is exposed to the pH-indicating solution by immersing the PCB in the pH-indicating solution. Any exposed laminate (PTH void) will cause the pH-indicating solution to undergo a color change at the surface of the PCB. The color change appears at each of the locations where exposed laminate (PTH voids) is present. Through backlighting or some similar technique, the plated through holes can be scanned for a color change using optical scanner 143.

The pH-activating compound can be covalently bound to a siloxane. A representative example is 1,10-phenanthrolyl-bis (4,7-diphenyl-1,10-phenanthrolyl)ruthenium II chloride disclosed in U.S. Pat. No. 5,070,158. The siloxane can then be bound to the exposed glass fiber in a PTH void. Upon immersion in a pH-indicating solution, such as an aqueous bath containing a pH-indicating dye, the pH-indicating solution reacts with the bound pH-activating compound. Once bonded to the Bronsted acid or base, the pH-indicator undergoes a color change that is detected by optical scanner 143.

In another embodiment, water soluble ammonium siloxane compositions are utilized, such as those disclosed in U.S. Pat.

No. 5,707,434. In this case, a base (the ammonium siloxane) is bound to exposed glass fibers in a PTH void. Upon exposure to (e.g., immersion in, etc.) a pH-indicating solution, such as an aqueous bath containing a pH-indicating dye, a color change results at the PCB surface locations where the PTHs are found. In one embodiment, these color changes are detected by optical scanner 143.

Figure 6:
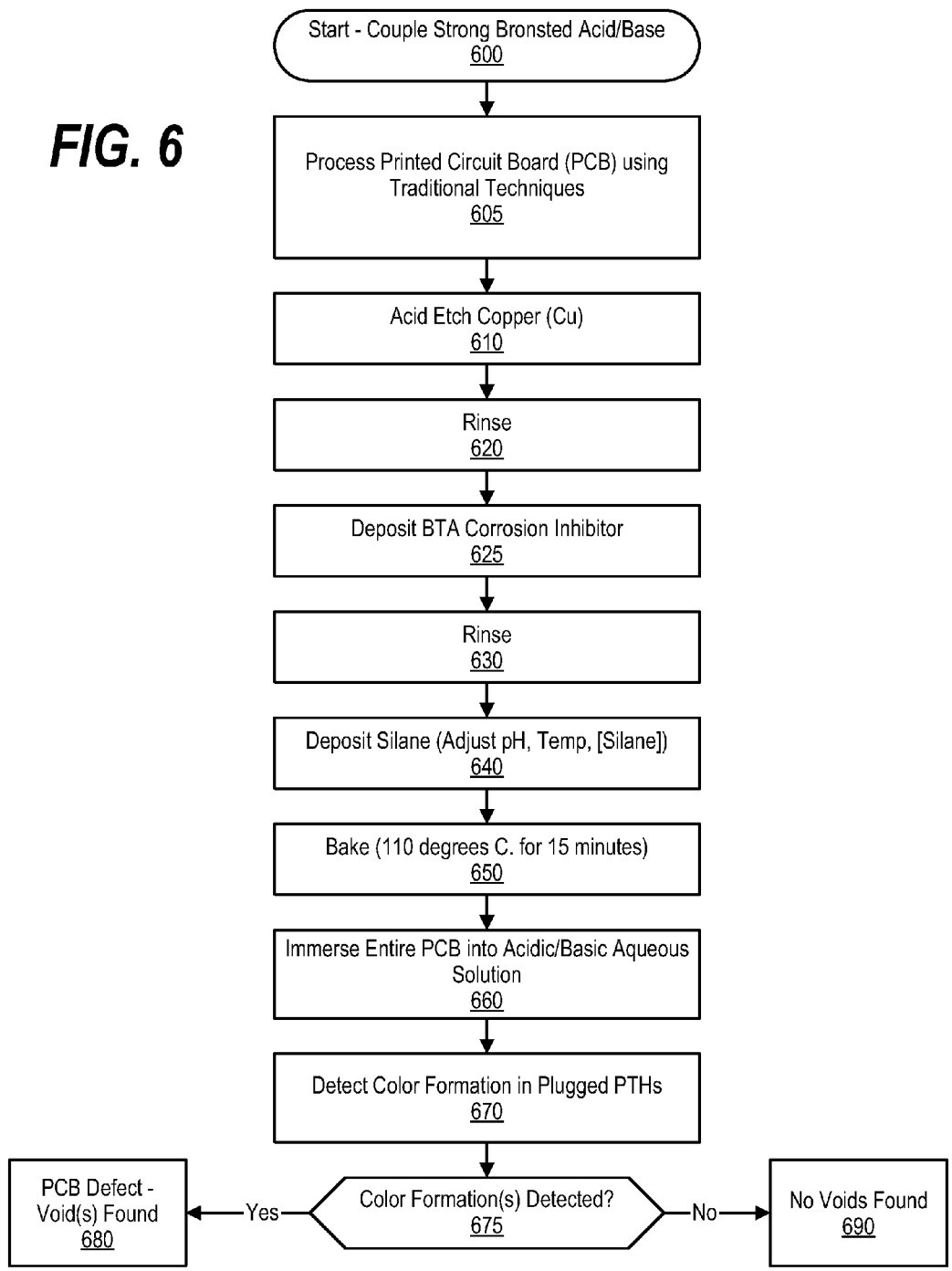
FIG. 6 is a flowchart showing steps taken to detect voids in a PCB that has a strong Bronsted acid or base coupled to the glass fiber surface of the PCB as shown in FIG. 5.

FIG. 6 is a flowchart showing steps taken to detect voids in a PCB that has a pH-activating compound, such as a strong Bronsted acid or base, coupled to the glass fiber surface of the PCB as shown in FIG. 5. Processing commences at 600 whereupon, at step 605, the PCB having the Bronsted acid-base previously coupled to the glass fiber layer of the PCB is processed using traditional techniques. One of these traditional processing steps includes laminating a conductive sheet (e.g., a thin sheet of copper, etc.) onto an outer surface of the PCB. At step 610, the conductive sheet is acid etched to remove oxides. At step 620, the PCB is rinsed. At step 625, in one embodiment, the conductive (e.g., copper) sheet is deposited (coated) with a corrosion inhibitor, such as benzotriazole (BTA). The corrosion inhibitor coats the exposed conductive layer (copper) and prevents subsequent chemisorption of the silane. At step 640, the PCB is deposited with silane by immersing in an aqueous silane bath whose parameters (temperature, pH, and silane concentration) are adjusted to deposit a sufficient layer of silane on any exposed glass fiber bundle ends that are present in any plated-through-hole defects in the PCB. At step 650, the PCB, having been exposed to (e.g., immersed in, etc.) the silane solution, is baked (e.g., at 110 degrees centigrade for approx. fifteen minutes, etc.). At step 660, the PCB is exposed to a pH-indicating solution which is an aqueous indicator solution designed to react with the pH-activating compound that was coupled to the glass fiber layer of the PCB. The pH-indicating solution binds with the pH-activating compound that is bound to the exposed glass fiber layer of the PCB.

At step 670, color formations on the PCB are detected. In one embodiment, the entire PCB is backlit using traditional backlighting techniques and color formation in plugged plated-through holes (PTHs) are detected either manually (visually), or using an optical color scanner that is connected to an information handling system. A decision is made as to whether color formations are detected (decision 675). If color formations are detected, then decision 675 branches to the "yes" branch whereupon, at step 680, the PCB is noted as being defective due to the presence of one or more plated-through-hole defects. On the other hand, if no color formations are detected, then decision 675 branches to the "no" branch whereupon, at step 690, the PCB is noted as not having any plated-through-hole defects.

While particular embodiments of the present disclosure have been shown and described, it will be obvious to those skilled in the art that, based upon the teachings herein, that changes and modifications may be made without departing from this disclosure and its broader aspects. Therefore, the appended claims are to encompass within their scope all such changes and modifications as are within the true spirit and scope of this disclosure. Furthermore, it is to be understood that the disclosure is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

The invention claimed is:

1. An apparatus including a printed circuit board, the printed circuit board comprising:
   a plurality of layers, wherein a pH-indicating compound is incorporated in one of the layers;
   a conductive sheet laminated onto an outer one of the plurality of layers; and
   a plurality of conductive pathways formed from the conductive sheet; wherein the printed circuit board is tested by exposing the printed circuit board to a pH-activating solution that identifies a plated-through hole defect at a surface location of the printed circuit board, wherein the surface location is identified by detecting a color formation at the surface location.

2. The apparatus of claim 1 wherein the color formation forms at a plugged aperture, and wherein the plugged aperture corresponds to the plated-through hole defect.

3. The apparatus of claim 1 wherein the pH-indicating compound is an organically modified silicate that includes a pH-sensitive dye, and wherein the pH-activating solution is a pH-non-neutral solution.

4. The apparatus of claim 3 wherein the organically modified silicate is formulated directly into a resin system of the printed circuit board.

5. The apparatus of claim 1 wherein one of the layers is a glass fiber layer, wherein the pH-indicating compound is a pH-sensitive dye that is covalently bound to a siloxane, wherein the siloxane bound to the pH-sensitive die is bound to the glass fiber layer.

6. The apparatus of claim 1 wherein the detection of the color change is performed by an optical scanner that is connected to an information handling system.

7. The apparatus of claim 1 further comprising a memory and a processor, wherein the apparatus is a computer system.

8. A printed circuit board comprising:
   a plurality of layers, wherein a pH-activating compound is incorporated in one of the layers;
   a conductive sheet laminated onto an outer one of the plurality of layers; and
   a plurality of conductive pathways formed from the conductive sheet; wherein the printed circuit board is tested by exposing the printed circuit board to a pH-activating solution that identifies a plated-through hole defect at a surface location of the printed circuit board, wherein the surface location is identified by detecting a color formation at the surface location.

9. The printed circuit board of claim 8 wherein the color formation forms at a plugged aperture, and wherein the plugged aperture corresponds to the plated-through hole defect.

10. The printed circuit board of claim 8 wherein one of the layers is a glass fiber layer, wherein the pH-activating compound is a Bronsted non-neutral compound that is coupled to the glass fiber layer, and wherein the pH-indicating solution is an aqueous solution with a pH-sensitive indicator.

11. The printed circuit board of claim 8 wherein one of the layers is a glass fiber layer, wherein the pH-activating compound is a water soluble ammonium siloxane composition that is coupled to the glass fiber layer, and wherein the pH-indicating solution is an aqueous solution with a pH-sensitive indicator.

\* \* \* \* \*